United States Patent [19]

A'Court

[11] Patent Number: 4,797,487

[45] Date of Patent: Jan. 10, 1989

[54] PRODUCTION OF BICYCLIC GUANIDINES FROM BIS(AMINOALKYL)AMINE

[75] Inventor: Richard A'Court, Beverley, England

[73] Assignee: BP Chemicals Ltd., London, England

[21] Appl. No.: 848,819

[22] Filed: Apr. 4, 1986

[30] Foreign Application Priority Data

Apr. 13, 1985 [GB] United Kingdom ............... 8509531

[51] Int. Cl.$^4$ .................................... C07D 487/04
[52] U.S. Cl. ................................ 544/279; 548/324
[58] Field of Search ....................... 544/279; 548/324

[56] References Cited

U.S. PATENT DOCUMENTS 3,865,836 2/1975 Van Gelder et al. ............... 548/315
3,923,808 12/1975 Van Gelder et al. ............... 544/279

OTHER PUBLICATIONS

Van Gelder et al. Chemical Abstracts, vol. 81, 77962v (1974).
Franz P. Schmidtchen, Chem. Ber., 113, 2175–2182 (1980).
Franz P. Schmidtchen, Chemical Abstracts, 93:95237q (1980).

Primary Examiner—Donald G. Daus
Assistant Examiner—E. Bernhardt
Attorney, Agent, or Firm—Brooks Haidt Haffner & Delahunty

[57] ABSTRACT

Bicyclic guanidines, useful as catalysts in a variety of chemical reactions, are produced by reacting a bis-(aminoalkyl)amine at ambient or elevated temperature with a compound of the formula $CX_2$ (I) or $(R^1)(R^2)CX$ (II) wherein in the formulae (I) and (II) X is either oxygen or sulphur and $R^1$ and $R^2$ in the formula (II) are independently either halogen atoms, $-NH_2$ groups, or alkoxide groups, for example carbon disulphide.

4 Claims, No Drawings

PRODUCTION OF BICYCLIC GUANIDINES FROM BIS(AMINOALKYL)AMINE

The present invention relates to the production of guanidines. In particular, the invention relates to a one step process for the production of bicyclic guanidines, for example 1,5,7-Triazabicyclo[4.4.0]dec-5-ene (TBD), which can be used as catalysts for a wide range of chemical reactions.

It is now established that bicyclic guanidines are extremely active and selective catalysts for a number of chemical reactions. Thus our European patent application publication No. 0110629 discloses a carboxylic or carbonic acid ester transesterification process using a bicyclic guanidine catalyst, while our European patent applications publication Nos. 0150106, 0150962, 0152240 and 0152241 disclose respectively the use of bicyclic guanidines as catalysts for the preparation of alkoxyalkyl esters, the reaction of dialkyl carbonates and 1,2-alkanediol dicarboxylates, the transesterification of urethanes and the transetherification of silyl ethers.

An important consideration in the commercial exploitation of bicylic guanidines as catalysts for any reaction is that the bicyclic guanidine be cheap to buy and easy to produce. Published syntheses of bicyclic guanidines have to date been complicated and have involved either the use of more than one step in the synthesis or have involved the use of prohibitively expensive starting materials. These problems are illustrated by the example in the Canadian Journal of Chemistry (1957) 35 1438 which involves a six step synthesis from 1,3-diaminopropane and carbon disulphide and Chem. Ber. (1980) 113 2175 which, although disclosing a one step synthesis of TBD hydrobromide, uses amongst its starting materials the prohibitively expensive tetramethylorthocarbonate and hydrobromic acid.

A one step process for the production of bicyclic guanidines has now been developed which has the advantage of using cheap starting materials. It has the further advantages of producing the bicyclic guanidine in high yields under mild conditions.

Accordingly, the present invention provides a process for the production of bicyclic guanidines which process comprising reacting a bis(aminoalkyl) amine at ambient or elevated temperature with a compound of the formula $CX_2$ (I) or $(R^1)(R^2)CX$ (II) wherein in the formula (I) and (II) X is either oxygen or sulphur and $R^1$ and $R^2$ in the formula (II) are independently either halogen atoms, $-NH_2$ groups, or alkoxide groups.

By the term bis(aminoalkyl) amine is meant a compound having the formula $H_2N(CR^3R^4)_nNH(CR^5R^6)_mNH_2$ (III) wherein n and m are integers having independently a value in the range from 2 to 6 and wherein $R^3$, $R^4$, $R^5$ and $R^6$ are independently hydrogen or substituted or unsubstituted alkyl or aryl groups. In addition the composition of each individual $-CR^3R^4-$ and $-CR^5R^6-$ unit may also differ for example by having differing $R^3$ and $R^5$ groups in each unit. Suitable bis(aminoalkyl) amines are those where $R^3$, $R^4$, $R^5$ and $R^6$ are independently hydrogen or a $C_1-C_3$ alkyl group. Preferred bis(aminoalkyl) amines are those in which $R^3$, $R^4$, $R^5$ and $R^6$ are hydrogen e.g. bis(2-aminoethyl)amine, $H_2N(CH_2)_2NH(CH_2)_2NH_2$, and bis(3-aminopropyl)amine, $H_2N(CH_2)_3NH(CH_2)_3NH_2$. When bis(3-aminopropyl)amine is used, the product bicyclic guanidine is TBD.

As regards the other reactant this is either a molecule of formula $CX_2$ or of formula $(R^1)(R^2)CX$ where X is either oxygen or sulphur and $R^1$ and $R^2$ are independently halogen atoms, $-NH_2$ groups or alkoxide groups. Preferred examples include carbon disulphide, phosgene and thiophosgene, of which carbon disulphide is most preferred.

The process described above is conveniently carried out in a solvent which does not react with either of the two reactants. Suitable solvents include high boiling hydrocarbons for example xylene.

In addition to the components described above, an acid catalyst can be added to improve the yield further. Any acid including mineral acids, organic acids and Lewis acids can be used. Preferred acids include sulphonic acids, such as methanesulphonic acid, p-toluenesulphonic acid and triflic acid, and Lewis acids.

Operation of the process described hereinbefore produces, in addition to the bicyclic guanidine, either two molecules of $H_2X$ per molecule of bicyclic guanidine formed or one molecule of $H_2X$ and one molecule each of $R^1H$ and $R^2H$. Thus in the case where carbon disulphide is used as a reactant, two molecules of hydrogen sulphide are produced as co-product. The co-product is in general volatile under the reactions conditions and hence can be removed overhead from the reaction vessel.

The process as described above is suitably carried out at elevated temperatures in the range from 10° to 200° C., preferably from 50° to 150° C.

The process can be carried out either batchwise or continuously.

The invention is now illustrated by reference to the following Examples.

EXAMPLE 1

Carbon disulphide (0.7 g) was added dropwise to a stirred solution of bis(3-aminopropyl)amine (1.3 g) in xylene (150 ml) at such a rate that the temperature of the solution did not exceed 50° C. The solution was heated under reflux in an atmosphere of nitrogen until evolution of hydrogen sulphide ceased. The hot supernatant liquid was decanted into a flask and cooled at room temperature under nitrogen. On cooling 1.1 g (79% yield) of TBD crystallised from the supernatant liquid as a white solid.

EXAMPLE 2

Carbon disulphide (0.7 g) was added dropwise to a stirred solution of bis(3-aminopropyl)amine (1.3 g) and p-toluenesulphonic acid (0.02 g) in xylene (150 ml) at such a rate that the temperature of the solution did not exceed 50° C. The solution was heated under reflux in an atmosphere of nitrogen until evolution of hydrogen-sulphide ceased. The hot supernatant liquid was decanted into a flask and cooled to room temperature under nitrogen. On cooling a white solid separated. This was filtered and dried to give white crystals, 1.2 g (86% yield); melting point, $^1H$ and $^{13}C$ nmr consistent with TBD.

EXAMPLE 3

Carbon disulphide (7.6 g) was added dropwise to a stirred solution of bis(2-aminoethyl)amine (10.3 g) and para-toluenesulphonic acid (1.5 g) in xylene (150 ml) at such a rate that the temperature of the solution did not exceed 50° C. The solution was heated under reflux in an atmosphere of nitrogen until evolution of hydrogen sulphide ceased. The hot supernatant liquid was decanted from the solid residue, and the solvent stripped under reduced pressure, to give an off-white solid (6.3 g) (56.7% yield) having a melting point, $^1$H and $^{13}$C n.m.r. consistent with 1,4,6-triazabicyclo(3.3.0)oct-4-ene (TBO).

I claim:

1. A process for the production of bicyclic guanidines which process comprises reacting in one step a bis-(aminoalkyl)amine selected from the group consisting of bis(2-aminoethyl)amine and bis(3-aminopropyl)amine, at a temperature in the range from 10° to 200° C., with carbon disulphide and in a high boiling hydrocarbon solvent.

2. A process according to claim 1 wherein there is added an acid catalyst selected from mineral acids, organic acids and Lewis acids.

3. A process according to claim 2 wherein the acid catalyst is a sulphonic acid which is either methanesulphonic acid, p-toluenesulphonic acid or triflic acid.

4. A process according to claim 1 wherein the elevated temperature is in the range from 50° to 150° C.

* * * * *